United States Patent
Fujii et al.

(10) Patent No.: US 11,666,928 B2
(45) Date of Patent: Jun. 6, 2023

(54) VORTEX RING GENERATION DEVICE

(71) Applicant: DAIKIN INDUSTRIES, LTD., Osaka (JP)

(72) Inventors: Chiho Fujii, Osaka (JP); Chie Emura, Osaka (JP); Yousuke Imai, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 17/226,701

(22) Filed: Apr. 9, 2021

(65) Prior Publication Data
US 2021/0220844 A1 Jul. 22, 2021

Related U.S. Application Data

(63) Continuation of application No. PCT/JP2019/040248, filed on Oct. 11, 2019.

(30) Foreign Application Priority Data

Oct. 12, 2018 (JP) .............................. JP2018-193429

(51) Int. Cl.
*B05B 1/06* (2006.01)
*F24F 13/06* (2006.01)
*A61L 9/12* (2006.01)

(52) U.S. Cl.
CPC .................. *B05B 1/06* (2013.01); *A61L 9/12* (2013.01); *F24F 13/06* (2013.01)

(58) Field of Classification Search
CPC .... B05B 1/06; A61L 9/12; F24F 13/06; F24F 2221/46; B60H 1/3457
USPC ....................................................... 454/329
See application file for complete search history.

(56) References Cited

U.S. PATENT DOCUMENTS 5,181,475 A * 1/1993 Breen ....................... F23C 1/00 110/212
8,523,642 B2 * 9/2013 Ezaka ..................... A61L 9/015 454/156
10,060,424 B2 * 8/2018 Fujiwara ................. F04B 43/04

FOREIGN PATENT DOCUMENTS

| JP | 2006-280748 A | 10/2006 |
| JP | 2008-18394 A | 1/2008 |
| JP | 2012-168890 A | 9/2012 |
| JP | 2016-90094 A | 5/2016 |
| JP | 2017-198433 A | 11/2017 |
| JP | 2018-42758 A | 3/2018 |
| JP | 2018-45106 A | 3/2018 |

OTHER PUBLICATIONS

International Search Report of corresponding PCT Application No. PCT/JP2019/040248 dated Dec. 10, 2019.
(Continued)

*Primary Examiner* — Allen R. B. Schult
(74) *Attorney, Agent, or Firm* — Global IP Counselors, LLP

(57) ABSTRACT

A vortex ring generation device includes a casing and an extrusion mechanism. The casing has a gas passage and a discharge port. The extrusion mechanism extrudes gas in the gas passage such that the gas in a vortex ring shape is discharged from the discharge port. V ($m^3$) represents an extrusion volume, D (m) represents a diameter of the discharge port, L (m) represents a length of a cylinder having the diameter D and the volume V, and U (m/s) represents a discharge flow rate $0.045 \leq D \leq 0.135$, $0.15 \leq L \leq 0.35$, and $3 \leq U \leq 5$.

2 Claims, 4 Drawing Sheets

(56) References Cited

OTHER PUBLICATIONS

International Preliminary Report of corresponding PCT Application No. PCT/JP2019/040248 dated Apr. 22, 2021.
European Search Report of corresponding EP Application No. 19 87 1287.9 dated Sep. 29, 2021.
Krieg Michael et al., "On Approximating the Translational Velocity of Vortex Rings", Journal of Fluids Engineering, Dec. 2013, Vaol. 135.

* cited by examiner

VORTEX RING GENERATION DEVICE

CROSS-REFERENCE TO RELATED APPLICATIONS

This is a continuation of International Application No. PCT/JP2019/040248 filed on Oct. 11, 2019, which claims priority to Japanese Patent Application No. 2018-193429, filed on Oct. 12, 2018. The entire disclosures of these applications are incorporated by reference herein.

BACKGROUND

Field of Invention

The present disclosure relates to a vortex ring generation device.

Background Information

Japanese Unexamined Patent Publication No. 2008-018394 discloses a device that generates a vortex ring and supplies the vortex ring containing, for example, a scent component to a predetermined region. The device according to Japanese Unexamined Patent Publication No. 2008-018394 is configured such that a vortex ring and straight flow running through the inside of the vortex ring are generated.

SUMMARY

A first aspect of the present disclosure is directed to a vortex ring generation device that includes a casing and an extrusion mechanism. The casing has a gas passage and a discharge port. The extrusion mechanism extrudes gas in the gas passage such that the gas in a vortex ring shape is discharged from the discharge port. V (m³) represents an extrusion volume, D (m) represents a diameter of the discharge port, L (m) represents a length of a cylinder having the diameter D and the volume V, and U (m/s) represents a discharge flow rate $0.045 \leq D \leq 0.135$, $0.15 \leq L \leq 0.35$, and $3 \leq U \leq 5$.

DETAILED DESCRIPTION OF EMBODIMENT(S)

Figure 1:
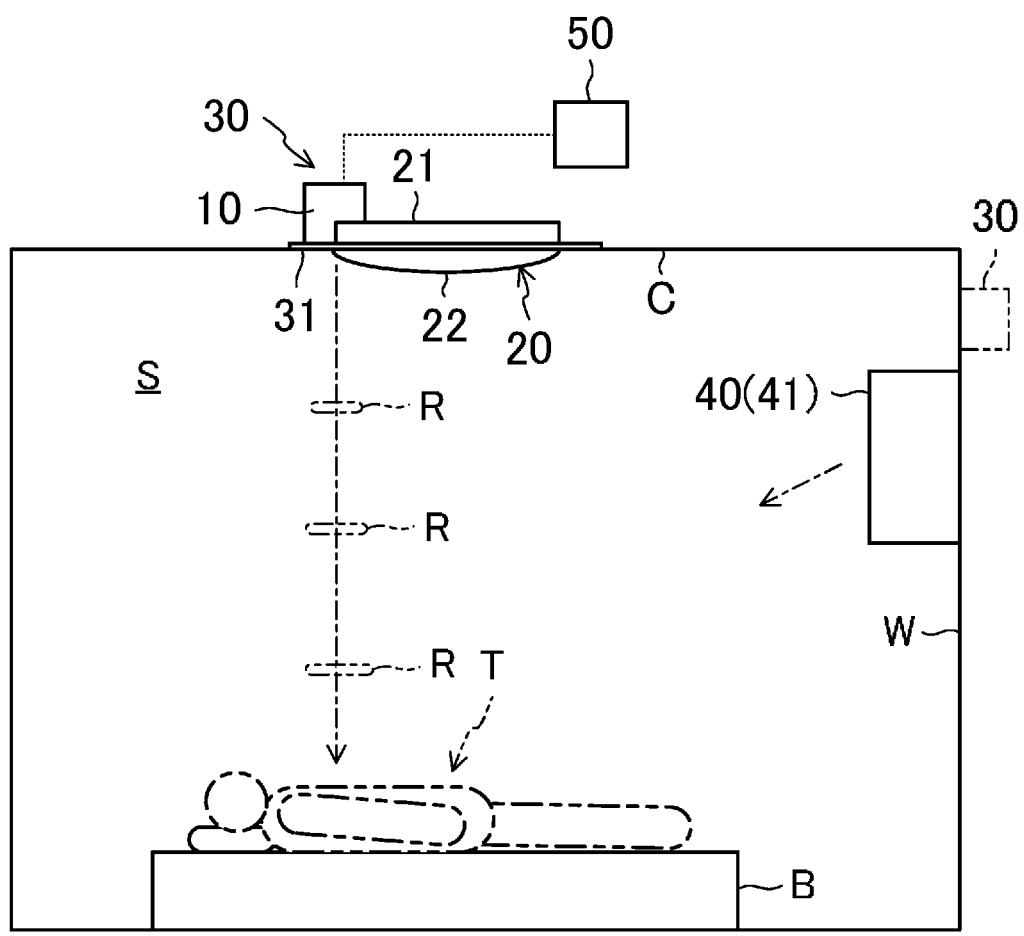
FIG. 1 is a diagram schematically illustrating an arrangement of components in a room in which a vortex ring generation device of an embodiment is provided.

Hereinafter, an embodiment of the present disclosure will be described with reference to the drawings. The embodiment described below is merely an exemplary one in nature, and is not intended to limit the scope, applications, or use of the invention.

The vortex ring generation device (10) of this embodiment is configured to supply a vortex ring containing a scent component to, for example, a sleeping person (T). According to FIGS. 1 and 2, the sleeping person sleeps on bedclothes such as a bed, in an indoor space (S) of a room that is a target space, for example. The indoor space (S) is provided with an air current generation unit (30) in which the vortex ring generation device (10) and an illumination device (20) are integral with each other, and an air-conditioning device (40). A controller (50) is connected to the air current generation unit (30).

The air-conditioning device (40) performs air conditioning of the indoor space (S). The air-conditioning device (40) includes, for example, an indoor unit (41) of wall-mounted type to be attached in a wall (W). The indoor unit (41) is connected to an outdoor unit (not shown) via a refrigerant pipe. The air-conditioning device (40) cools or heats indoor air (room air) depending on a refrigerant with which a refrigeration cycle is performed. In this manner, the temperature of air in the indoor space (S) is adjusted. The air-conditioning device (40) may be capable of adjusting the humidity of the indoor air (room air) in addition to the temperature thereof.

Figure 3:
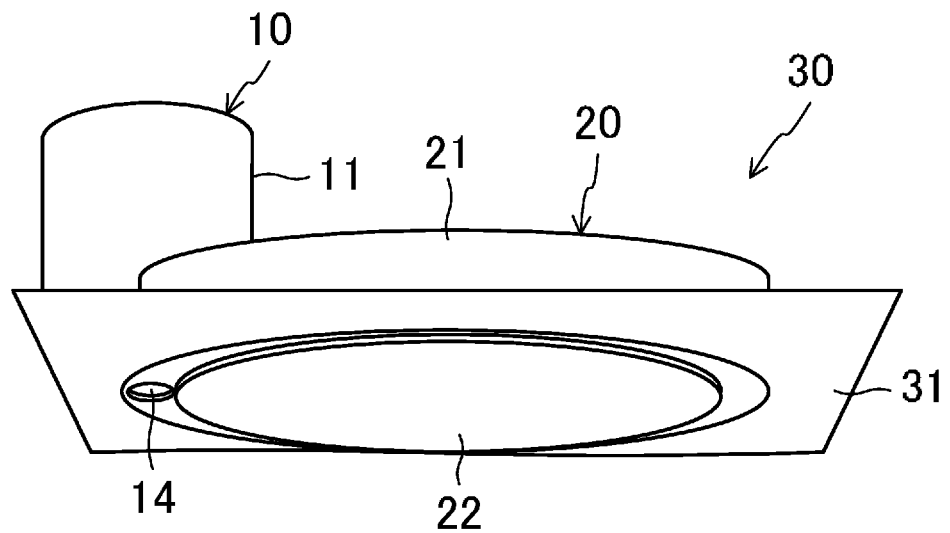
FIG. 3 is a perspective view of an air current generation unit.

As shown in FIGS. 1 and 3, the air current generation unit (30) includes a fixation plate (31), the vortex ring generation device (10), and the illumination device (20) that are unitized. The fixation plate (31) is formed into a shape of a horizontal flat plate and arranged on a back surface of a ceiling (C), for example. The illumination device (20) includes an illumination body (21) and a cover (22) detachably attached to a lower part of the illumination body (21). The illumination body (21) includes a light source such as an LED and a circuit board having a dimming circuit (not shown) for adjusting light of the light source mounted thereon. The cover (22) is made from a resin material having translucency and exposed to the indoor space (S).

Figure 4:
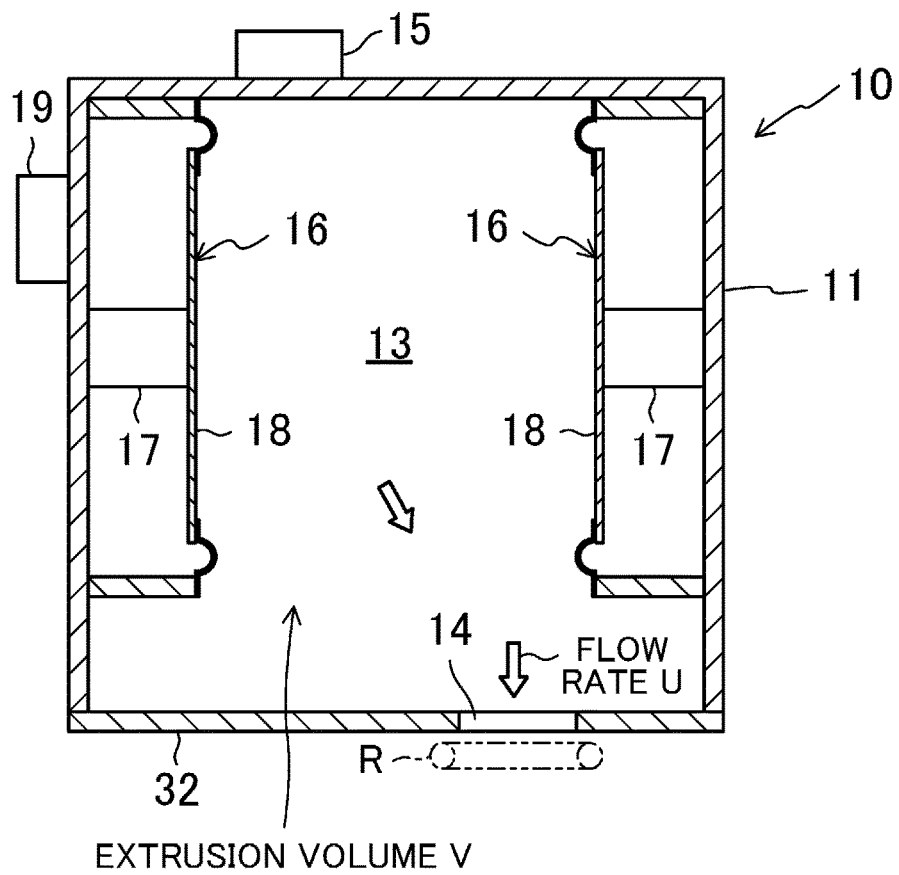
FIG. 4 is a longitudinal cross-sectional view of the vortex ring generation device.

As shown in FIG. 4, the vortex ring generation device (10) includes: a tubular casing (11) having lower side open; and a lower lid (12) covering the lower opened side of the casing (11). The casing (11) includes, in its inside, an air passage (gas passage) (13). The lower lid (12) is provided with a discharge port (14) communicating with the air passage (13). The discharge port (14) is opened toward the indoor space (S). The discharge port (14) faces down 10 to be directed to the sleeping person (T). The fixation plate (31) is installed in the ceiling (C). Accordingly, the casing (11) of the vortex ring generation device (10) is also installed in the ceiling (C) of the room forming the indoor space (s) in which vortex-like air is discharged.

The vortex ring generation device (10) includes a component supply device (15). The component supply device (15) supplies, to the air passage (13) inside the casing (11), a predetermined discharge component such as a scent component that gives scent to the vortex ring (R). Although not shown, the component supply device (15) includes a component generation unit that generates the discharge component and a conveyance unit that conveys the discharge component generated in the component generation unit. The component generation unit is, for example, of a vaporizing type that vaporizes the discharge component from a component raw material. The conveyance unit is, for example, an air pump. The component supply device (15) appropriately supplies, to the air passage (13), the discharge component whose concentration has been adjusted to a predetermined concentration.

The casing (11) includes therein a plurality of extrusion mechanisms (16). Each of the extrusion mechanisms (16)

extrudes air of the air passage (13) such that the air of the air passage (13) is discharged in a shape of vortex ring from the discharge port (14). The vortex ring generation device (10) includes eight extrusion mechanisms (16), as apparent from the horizontal cross section of the vortex ring generation device (10) in FIG. 4. Each of the extrusion mechanisms (16) includes a linear actuator (17) that is a driving unit and a vibration plate (18) that is driven by the linear actuator (17). The linear actuator (17) displaces the vibration plate (18) back and forth (in a direction perpendicular to the plane of the vibration plate (18)). In this embodiment, the plurality of extrusion mechanisms (16) are arranged along a peripheral wall of the casing (11). The extrusion mechanisms (16) are arranged circumferentially at equal spaces. As describes above, the extrusion mechanisms (16) includes a plurality of vibration plates (18) that changes the volume of the air passage (13) and extrudes gas of the air passage (13) when the volume is reduced.

As shown in FIG. 4, the vortex ring generation device (10) includes a drive control unit (19) that controls the extrusion mechanisms (16). The drive control unit (19) includes a circuit board to be connected to the linear actuator (17). The drive control unit (19) is arranged, for example, outside the casing; however, it may be arranged inside the casing (11). The drive control unit (19) is configured to adjust the amplitude of vibrations of the vibration plates (18) and the cycles of the vibrations.

The controller (50) includes a microcomputer and a memory device storing software for operating the microcomputer (specifically, a semiconductor memory). The controller (50) is connected to the vortex ring generation device (10) via wires or wirelessly to control the vortex ring generation device (10). The controller (50) may be connected to the illumination device (20) and the air-conditioning device (40) to control these devices.

The controller (50) may be provided for the air current generation unit (30) or may be separate from the air current generation unit (30). For example, when the controller (50) is configured to perform air conditioning control as well, the controller (50) may be provided for a control unit or a remote controller of the air-conditioning device (40), or may be provided for a server connected to a local network or the Internet, or in various communication terminals (such as a mobile terminal and a personal computer).

Figure 5:
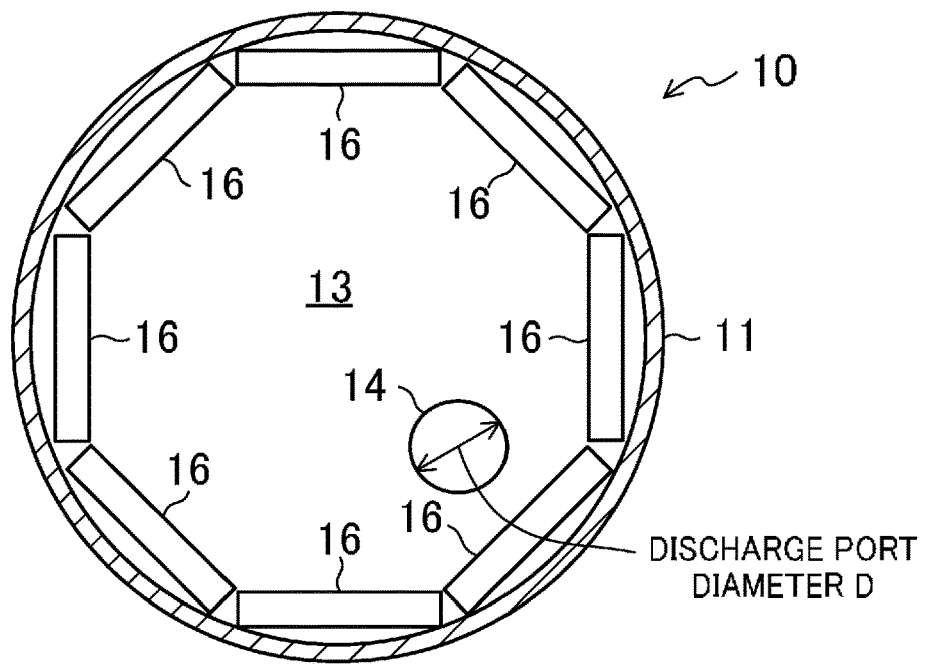
FIG. 5 is a horizontal cross-sectional view of the vortex ring generation device.
Figure 6:
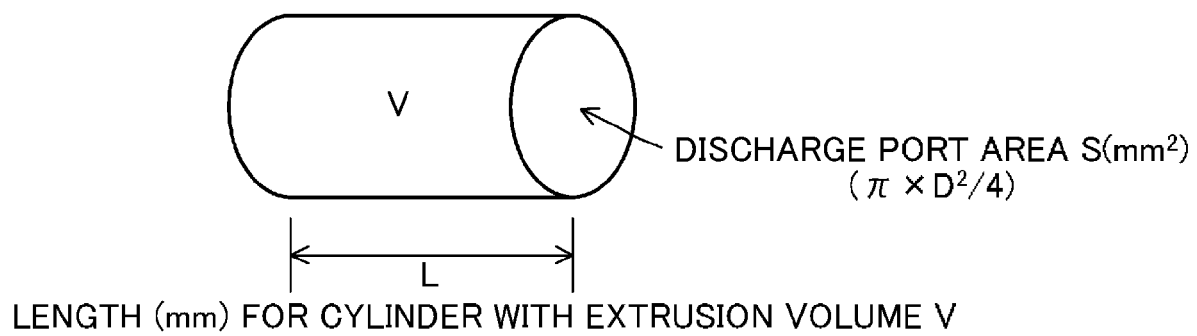
FIG. 6 is a perspective view of a cylinder having an extrusion volume V and an outlet diameter D.

In this embodiment, when that V ($m^3$) represents an extrusion volume (internal volume of the air passage (13)) shown in FIG. 4, D (m) represents a diameter of the discharge port (14) shown in FIG. 5, L (m) represents a length of a cylinder (cylinder equivalent length) having the diameter D and the volume V shown in FIG. 6, and U (m/s) represents a discharge flow rate, relationships of $0.045 \leq D \leq 0.135$, $0.15 \leq L \leq 0.35$ and $3 \leq U \leq 5$ are satisfied.

When the air current generation unit (30) including the vortex ring generation device (10) is installed in the ceiling (C), the diameter (D) of the discharge port (14) should satisfy a relationship of $0.045 \leq D \leq 0.075$. In the case of the installation in the ceiling, the outreach A of the vortex ring is approximately $1.5 \text{ m} \leq A \leq 2.5 \text{ m}$. This is because the relationship of $0.045 \leq D \leq 0.075$ is an appropriate range for the outreach A. Note that the ranges of U and L are the same as those stated above.

Operation

The operation of the vortex ring generation device (10) will be described.

When the vortex ring generation device (10) is operated, each of the vibration plates (18) of the extrusion mechanisms (16) is driven by the linear actuator (17). Each of the vibration plates (18) vibrates back and forth. Then, air containing a scent component is pushed toward the discharge port (14) when the volume of the air passage (13) is reduced. The air passing through the discharge port (14) has a relatively high flow rate, whereas the air around the discharge port is still. For this reason, a shearing force acts on the air at discontinuous planes of both air flows, and a vortex flow is generated adjacent to an outer circumferential edge of the discharge port (14).

Figure 2:
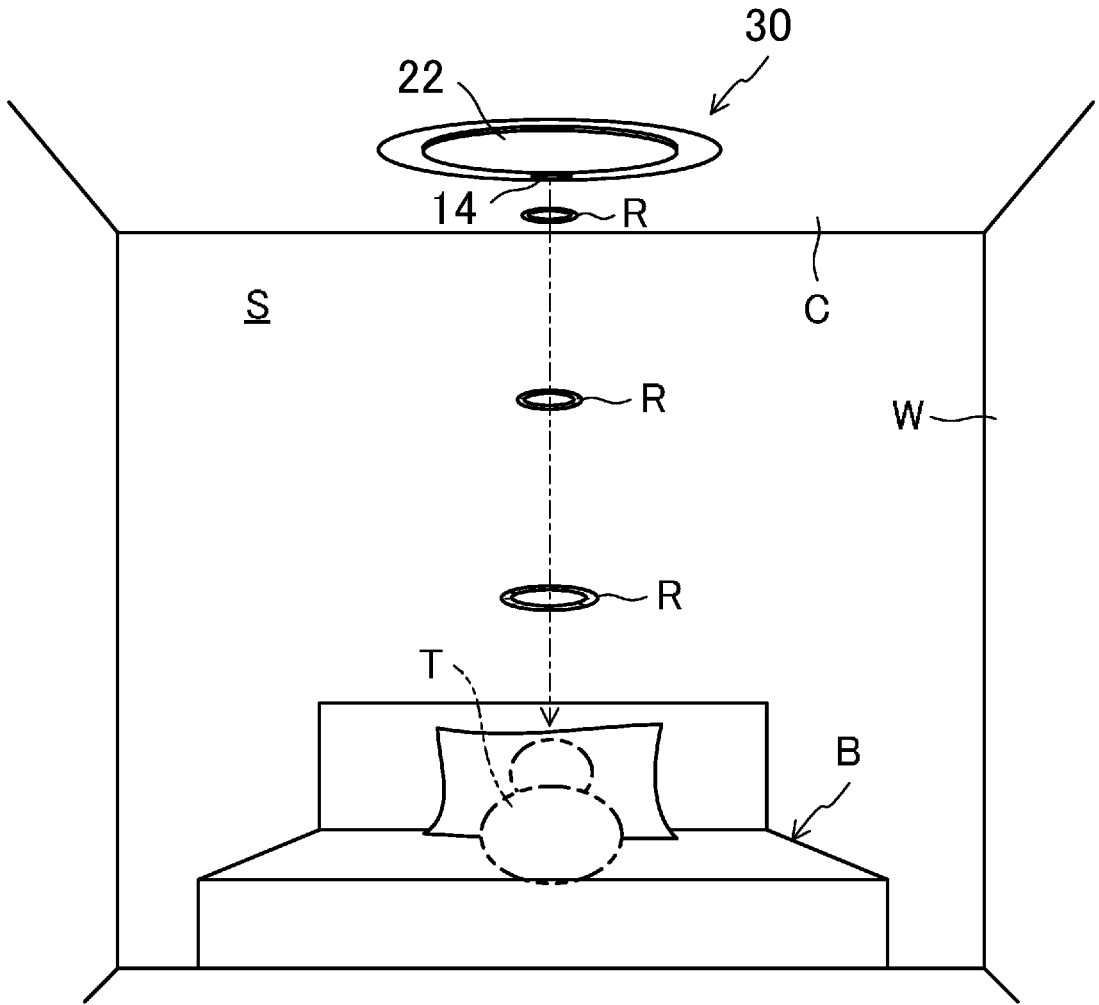
FIG. 2 is a perspective view of the inside of the room of FIG. 1 viewed from another direction.

With the vortex flow, an air current (vortex ring (R)) moving downward from the discharge port (14) is formed. FIGS. 1, 2 and 4 show this vortex ring (R) schematically. The vortex ring (R) discharged from the discharge port (14) flows downward to the sleeping person (T). The vortex ring (R) contains a scent component. The scent component thus reaches the sleeping person (T). This scent component can make the sleeping person experience, for example, a relaxing effect.

Advantages of First Embodiment

It has been difficult for known vortex ring generation devices to generate a stable vortex ring because they generate a straight flow inside the vertex ring. Further, even if the known vortex ring generation devices generate a vortex ring, the vortex ring moves together with the straight flow. Accordingly, the vortex ring is likely to disappear and the outreach becomes short. In addition, when the vortex ring contains a scent component, the scent component is dispersed and hardly reaches a sleeping person.

In the vortex ring generation device of this embodiment, the extrusion volume V (m), the diameter D (m) of the discharge port (14), the cylinder equivalent length L (m), and the discharge flow rate U (m/s) satisfy relationships of $0.045 \leq D \leq 0.135$, $0.15 \leq L \leq 0.35$, and $3 \leq U \leq 5$.

If D is smaller than 0.045 m (45 mm), the diameter of the vortex ring generated becomes too small. Accordingly, it becomes difficult to increase the outreach while maintaining the shape of the vortex rings. If D is larger than 0.135 m (135 mm), the diameter of the vortex rings generated becomes too large. Accordingly, the vortex ring is likely to be dispersed, and it becomes difficult to increase the outreach.

If L is smaller than 0.15 m (150 mm) or U is smaller than 3 m/s, the extrusion length is too short or the discharge flow rate is too slow. This causes insufficient generation of vortex flow around the outer circumferential edge of the discharge port (14), and a stable vortex ring is less likely to be generated. If L is larger than 0.35 m (350 mm) or U is larger than 5 m/s, the extrusion length is too long or the discharge flow rate is too fast. This causes the vortex flow generated around the outer circumferential edge of the discharge port (14) to be unstable, and a stable vortex ring is less likely to be generated.

According to this embodiment, the diameter D of the discharge port (14), the length L of the cylinder (cylinder equivalent length) having the diameter D and the volume V, and the discharge flow rate U are set in the above-stated ranges. This stabilizes the vortex flow generated around the outer circumferential edge of the discharge port (14), and makes a straight flow less likely to be generated, thereby generating a vortex ring. As a result, the outreach A of the vortex ring becomes approximately $1.5 \leq A \leq 5$ m. In the vortex ring generation device of this embodiment, a scent component is contained in the vortex ring. Accordingly, the scent component can be easily delivered to a sleeping person below the vortex ring generation device (10). Further, the flow rate of the vortex ring discharged is fast. This the vortex rings stimulates the person.

When the air current generation unit (30) including the vortex ring generation device (10) is installed in the ceiling (C), the diameter (D) of the discharge port (14) satisfies a relationship of 0.045≤D≤0.075. As a result, the vortex ring can be supplied to a person who is below the ceiling (C) by about 1.5 m to 2.5 m.

Variation of First Embodiment

In the above embodiment, the vortex ring generation device (10) is installed in the ceiling (C) and discharges a vortex ring downward. However, the site where the vortex ring generation device (10) is installed is not limited to the site described in the above embodiment. For example, as indicated by the two-dot chain line of FIG. 1, the vortex ring generation device (10) is installed in the wall (W) of a room and discharges a vortex ring (R) toward the side to deliver a scent component to the sleeping person. Further, the installation height of the vortex ring generation device (10) may be set as appropriate.

The vortex ring generation device (10) may be integral with the indoor unit (41). In this case, the indoor unit (41) may be provided with a blowout port of the vortex ring besides the discharge port of the conditioned air.

When the air current generation unit (30) including the vortex ring generation device (10) is installed in the wall (W), the diameter (D) of the discharge port (14) preferably satisfies a relationship of 0.045≤D≤0.060. In the case of the installation in the wall, the outreach A of the vortex ring is approximately 1.5 m≤A≤2.0 m. This is because the relationship of 0.045≤D≤0.060 is an appropriate range for the outreach A. Note that the ranges of U and L are the same as those stated above. As a result, the vortex ring can be supplied to a person who is below the wall (C) by about 1.5 m to 2.0 m.

Another Embodiment

The foregoing embodiment may also be configured as follows.

For example, the eight extrusion mechanisms (16) are provided in the vortex ring generation device (10) in the above embodiment. However, the number of extrusion mechanisms (16) is merely an example and may be one.

In the above embodiment, the vortex ring containing a scent component is supplied to a sleeping person. However, the component contained in the vortex ring may be any discharge component other than the scent component. In addition, only the vortex ring without any discharge component may be supplied to the sleeping person. Further, the target to which the vortex ring is supplied does not need to be a sleeping person. For example, the vortex ring generation device (10) may be installed in a wall (W) in a conference room or other venues to supply a vortex ring containing scent or the like toward the center of the indoor space.

In the above embodiment, the discharge port (14) of the vortex ring generation device (10) has a circular shape. However, the shape of the discharge port (14) is not limited to circular, and may be a polygon or any other shape as far as it has a hydraulic diameter equivalent to the diameter D.

While the embodiments and variations thereof have been described above, various changes in form and details may be made without departing from the spirit and scope of the claims. The embodiments and the variations thereof may be combined and replaced with each other without deteriorating intended functions of the present disclosure.

As described above, the present disclosure is useful for a vortex ring generation device.

The invention claimed is:

1. A vortex ring generation device, comprising:
a casing having a gas passage and a discharge port; and
an extrusion mechanism configured to extrude gas in the gas passage through the discharge port such that the gas in a vortex ring shape is discharged from the discharge port,
the extrusion mechanism including at least one vibration plate, each vibration plate including an actuator configured to change a volume of the gas passage and to extrude the gas of the gas passage when the volume is reduced, each vibration plate being fixed to the casing, each actuator moving the respective vibration plate in a direction perpendicular to the discharge port,
the casing being installed in a wall of a target space into which the gas in the vortex ring shape is discharged,
when V (m$^3$), which is a volume of the gas extruded through the discharge port when the gas passage is reduced, represents an extrusion volume, D (m) represents a diameter of the discharge port, U (m/s) represents a discharge velocity, and L (m) represents a length of an equivalent cylinder having the extrusion volume V and the diameter D,
0.045≤D≤0.060,
0.15≤L≤0.35, and
3≤U≤5.

2. The vortex ring generation device of claim 1, wherein the at least one vibration plate includes a plurality of vibration plates.

\* \* \* \* \*